(12) United States Patent
Halatsch et al.

(10) Patent No.: US 11,660,462 B2
(45) Date of Patent: May 30, 2023

(54) IMPLANT SYSTEM

(71) Applicants: Felix Capanni, New-Ulm (DE);
Marc-Eric Halatsch, Ulm (DE)

(72) Inventors: Marc-Eric Halatsch, Ulm (DE); Felix Capanni, Neu-Ulm (DE); Georg Karpel-Massler, Stuttgart (DE); Richard Eric Kast, Burlington, VT (US)

(73) Assignees: Marc-Eric Halatsch, Ulm (DE); Felix Capanni, Neu-Ulm (DE)

( * ) Notice: Subject to any disclaimer, the term of this patent is extended or adjusted under 35 U.S.C. 154(b) by 0 days.

(21) Appl. No.: 16/815,885

(22) Filed: Mar. 11, 2020

(65) Prior Publication Data

US 2020/0206525 A1    Jul. 2, 2020

Related U.S. Application Data

(63) Continuation of application No. PCT/EP2018/074039, filed on Sep. 6, 2018.

(30) Foreign Application Priority Data

Sep. 11, 2017   (DE) ............... 10 2017 120 949.2

(51) Int. Cl.
*A61N 5/06* (2006.01)

(52) U.S. Cl.
CPC ......... *A61N 5/0601* (2013.01); *A61N 5/0613* (2013.01); *A61N 2005/0626* (2013.01); *A61N 2005/0652* (2013.01)

(58) Field of Classification Search
CPC ............... A61N 5/0601; A61N 5/0613; A61N 2005/0626; A61N 2005/0652; A61N 5/062

See application file for complete search history.

(56) References Cited

U.S. PATENT DOCUMENTS

| 4,998,930 | A | * | 3/1991 | Lundahl | A61N 5/062 606/15 |
| 5,445,608 | A | * | 8/1995 | Chen | A61N 5/0601 604/19 |
| 6,071,302 | A | * | 6/2000 | Sinofsky | A61N 5/0601 606/15 |
| 8,382,812 | B2 | | 2/2013 | Kang et al. | |
| 10,751,544 | B2 | | 8/2020 | Lippert et al. | |

(Continued)

FOREIGN PATENT DOCUMENTS

| CN | 101744611 A | 6/2010 |
| CN | 202070026 U | 12/2011 |

(Continued)

OTHER PUBLICATIONS

International Search Report dated Dec. 3, 2018 in corresponding application PCT/EP2018/074039.

(Continued)

*Primary Examiner* — Carl H Layno
*Assistant Examiner* — Joshua Andrew Schum-Houck
(74) *Attorney, Agent, or Firm* — Muncy, Geissler, Olds & Lowe, P.C.

(57) ABSTRACT

An implant system for photodynamic therapy with a light source for radiating light which is implantable in a resection cavity, and with an autonomous control unit which is connectable via a supply line to the light source.

22 Claims, 3 Drawing Sheets

(56) References Cited

U.S. PATENT DOCUMENTS

| | | | |
|---|---|---|---|
| 2002/0087206 A1* | 7/2002 | Hirschberg | A61N 5/0601 607/89 |
| 2005/0192638 A1* | 9/2005 | Gelfand | A61N 1/3605 607/3 |
| 2006/0111762 A1 | 5/2006 | Sterenborg et al. | |
| 2007/0208395 A1* | 9/2007 | Leclerc | A61N 5/0616 607/86 |
| 2008/0033519 A1* | 2/2008 | Burwell | A61N 5/0601 607/122 |
| 2009/0054955 A1* | 2/2009 | Kopell | A61N 5/0601 607/88 |
| 2009/0171408 A1* | 7/2009 | Solem | A61N 1/3975 607/4 |
| 2010/0305666 A1 | 12/2010 | Lou et al. | |
| 2011/0125078 A1* | 5/2011 | Denison | A61N 5/0601 604/20 |
| 2011/0149591 A1* | 6/2011 | Smith | G02B 23/2469 362/555 |
| 2013/0317572 A1* | 11/2013 | Zhu | A61N 1/0551 607/89 |
| 2014/0128943 A1 | 5/2014 | Rogers et al. | |
| 2016/0030765 A1* | 2/2016 | Towne | A61N 5/0622 607/88 |
| 2016/0138763 A1* | 5/2016 | Liu | F21V 19/0045 362/249.02 |
| 2020/0206525 A1 | 7/2020 | Halatsch et al. | |

FOREIGN PATENT DOCUMENTS

| | | | |
|---|---|---|---|
| DE | 19819975 A1 | 11/1999 | |
| DE | 102014107298 A1 | 11/2015 | |
| EP | 1334748 A1 | 8/2003 | |
| RU | 2346712 C1 | 2/2009 | |
| WO | WO-2013055329 A1 * | 4/2013 | A61B 5/031 |
| WO | WO2019048559 A1 | 3/2019 | |

OTHER PUBLICATIONS

Chinese Office Action for Chinese Application No. 201800727756 dated Nov. 3, 2021 with partial English translation.

* cited by examiner

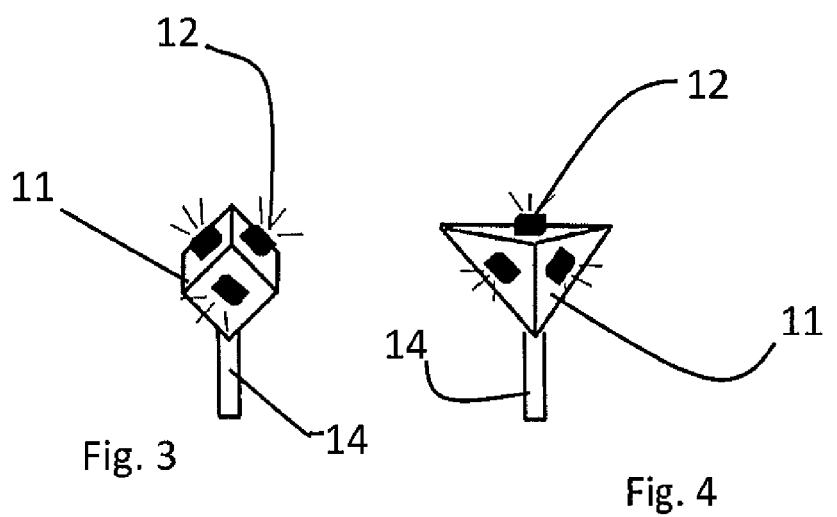
Fig. 3
Fig. 4
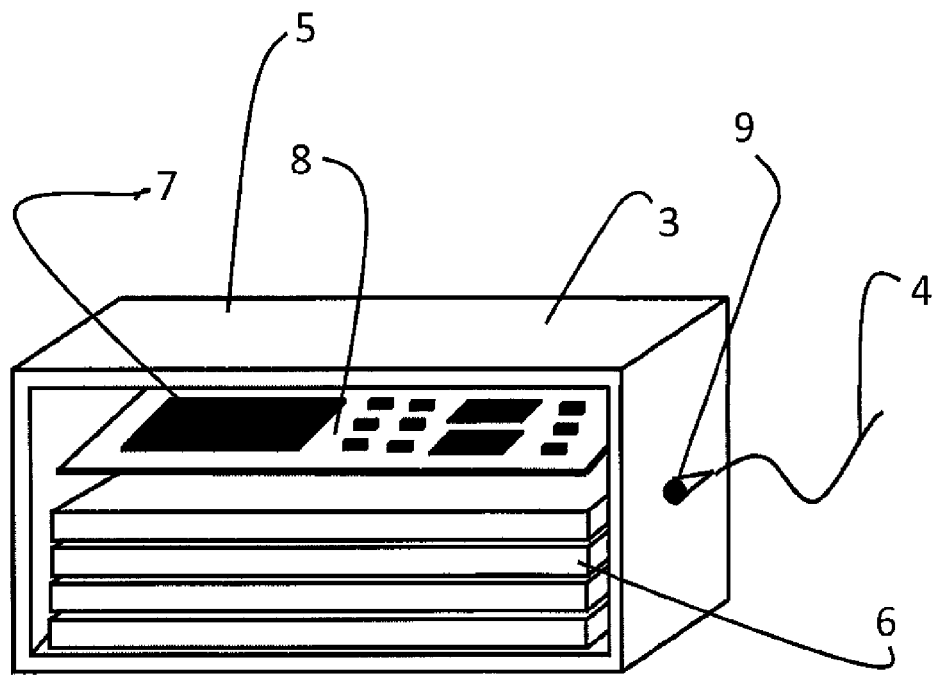
Fig. 5

IMPLANT SYSTEM

This nonprovisional application is a continuation of International Application No. PCT/EP2018/074039, which was filed on Sep. 6, 2018, and which claims priority to German Patent Application No. 10 2017 120 949.2, which was filed in Germany on Sep. 11, 2017, and which are both herein incorporated by reference.

BACKGROUND OF THE INVENTION

Field of the Invention

The present invention relates to an implant system for photodynamic therapy with a light source for radiating light that can be implanted in a resection cavity, and with an autonomous control unit which is connected via a supply line to the light source.

Description of the Background Art

Glioblastomas are the most common and most aggressive brain tumors in adults. An illness with such a malignant brain tumor is still not curable and the sick person has only an average survival time of about 16 months. A therapeutic approach is to surgically remove the malignant brain tumor in combination with intraoperative photodynamic therapy in which the patient is fed a drug which accumulates in the tumor cells as selectively as possible and has a phototoxic effect when irradiated with light of a suitable wavelength. The removal of the malignant tumor, whose position in the brain prevents precautionary ample removal of also healthy tissue, leaves behind a resection cavity with a resection margin in which malignant cells commonly remain. It is possible that by means of a lamp introduced through the open surgical wound into the resection cavity, the drug absorbed by the tumor cells is activated so as to destroy malignant cells remaining in the resection margin.

The disadvantage here is that this therapy option is only an option while operating in the open surgical wound and in order to avoid too much strain on the patient, the duration of the photodynamic therapy cannot be extended as needed.

SUMMARY OF THE INVENTION

It is therefore an object of the present invention to improve the applicability of photodynamic therapy so as to increase the mean survival time for patients with tumors.

This object is achieved by an implant system with which it is possible to implant a light source into the resection cavity created by the removal of the tumor, through which light with a therapeutically effective wavelength can be emitted so that through exposure of the tumor cells to light, which are enriched with a phototoxic drug, the photodynamic therapy can be continued even after the operation and after closing the surgical wound.

Since in principle any resection cavity is suitable, the application of the implant system is not limited to glioblastomas, but can also be expanded to include photodynamic therapy of, for example, tumors of the liver, pancreas, kidney, bladder, and prostate, bronchial carcinoma, ENT field head and neck tumors, mammary carcinomas after breast-conserving surgery with a high risk of recurrence, endometrium (cervical carcinomas after uterus-conserving resection in case of a desire to have children with a high risk of recurrence), among other things.

The chance of survival of the patient suffering from a glioblastoma is increased if early removal is possible, i.e. before the glioblastoma has grown significantly and the space associated therewith leaves behind a large resection cavity after removal of the glioblastoma. Thus, there is usually a relatively small resection cavity. To be able to power the light source for a long time, the autonomous control unit is provided which can also be arranged outside of the cranium, spatially separated from the light source, wherein the distance between the light source and the control unit can be measured over the length of the supply line. Both the supply line as well as the autonomous control unit can be arranged subcutaneously, intracorporeally and thus permanently implanted to complete the implant system.

Due to the spatial separation of the autonomous control unit from the light source, an adequate volume can be provided in the autonomous control unit, independent of the size of the resection cavity, for the power supply and control of the operating mode of the light source.

It is further provided that the light source is made from a translucent material, particularly transparent plastic or glass, and that, if appropriate, scattering centers for promoting uniform illumination are formed in the translucent material. The use of glass for optical purposes has proven successful; in particular, by way of low absorption it can be ensured that a sufficient luminous intensity is available to activate the phototoxic drug, even if the energy consumption is optimized to a minimum radiation of light in order to achieve a maximum light duration of the implant. There is no risk of breakage due to the placement of the light source in the brain and thus within the skull cap.

Another option to control the light radiation is given in particular if masking is provided on the light source for partial illumination.

The light source can be formed of two half shells, between which at least one light source is accommodated, which is connectable by means of the supply line with the voltage source arranged in the autonomous control unit.

The light source can also be provided in plurality and that each of the light sources are formed by an LED. LEDs are characterized by their long lifespan and low energy consumption, although there is usually a relatively small radiation angle. To achieve the preferred spherical radiation, this can be compensated by using multiple LEDs, wherein the arrangement of the LEDs is chosen to be one for a uniform spherical illumination. For this purpose, the LEDs are arranged on an LED carrier, which is configured to be the connecting link of the LEDs with the supply line. It has proven to be favorable when the LED carrier is the shape of a sphere, or the shape of a cuboid, including the special shape of a cube, or the shape of a pyramid, on the surfaces of which the LEDs are arranged in the center of gravity.

An improved way to fight tumors or tumor cells is if the control unit has a reservoir for a drug, the reservoir being connected via a drug line to the light source, which is set up to dispense the drug to the surrounding tissue. The provided drug can be the same used for the phototoxicity or be a supplementary drug. It is preferred when the drug line runs parallel to the supply line and the light source has pores and/or channels on its surface for distributing the drug, and when the reservoir comprises a drug absorption path for filling by means of an extracorporeal injection needle.

Two coupling links can be provided for the releasable connection of the supply line to the control unit, one of which one is disposed on the outer wall of the control unit housing. This offers advantages during operation when implanting the implant system, since it is possible to place the light source in the resection cavity created by the removal of the tumor and to then place the supply line subcutaneously in the patient's upper body. There, the connecting line is coupled with its associated coupling link to the coupling link disposed on the outer wall of the control unit housing.

Several light sources of different volumes can be provided for the optional connection of one of the light sources via the assigned supply line to the coupling link of the control unit. Thus, a modular implant system is provided in which the size of the light source can be adapted as closely as possible to the size of the resection cavity so as to allow for the direct radiation of light onto the resection margin of the brain facing the former tumor, without deposits/scarring forming between the surface of the light source and the margin during the healing process.

A plurality of light sources with light(s) of a different radiation frequency can be provided for the optional connection of one of the light sources via the assigned supply line to the coupling link of the control unit. This creates the possibility that for achieving a maximum phototoxic effect, the appropriate wavelengths are available to activate the adjustable drug. A light source emitting in the UV range at approx. 280 nm can also be used, in combination with light for phototoxic activation. The light in the UV range have a tumoricidal effect on the tumor resection margin even without phototoxic drugs.

The control unit can have at least one rechargeable electric memory cell for supplying power to the at least one LED and a control board, wherein the memory cell can be embodied as an accumulator which can be charged inductively, that is to say, in order to prolong the useful life of the implant system in the implanted state, a charge of the memory cell is possible without new surgical intervention. Also conceivable is an exchange of data between the implanted control unit and an extracorporeal transmitting and receiving unit, for example, to read out data regarding the treatment or the energy consumption from a memory associated with the control unit or to adapt the program to the control unit. The data exchange takes place wirelessly by radio, such as NFC or RFID.

The light source is relatively well protected inside the skull cap, while the control unit is normally subcutaneously positioned and thus exposed to outside influences. It is therefore provided that the housing of the control unit is made of implant steel or titanium or a biocompatible plastic, for example PEEK. Making the housing from plastic or with a plastic window favors the exchange of data via radio and the inductive charging of the memory cell in the control unit. Moreover, fewer artifacts are caused in imaging processes. It is also favorable if the light source and/or the supply line and/or the control unit and/or the drug line is coated with a biocompatible material, which may well be different from the biocompatible plastic. It has proven to be suitable for the coating if the biocompatible material is made of medical silicone.

With such an implant system it is possible that photodynamic therapy can be carried out over a long period of time, in particular because sufficiently large energy storage, optionally rechargeable, is provided due to the control unit spatially separated by the light sources and there continues to be sufficient space in the control unit to control the operation of the light source by means of microcontrollers on the control board. In this case, it is possible that the light source continuously radiates light or that the radiation of the light takes place in a clocked manner or that the intensity of the radiated light is varied over time. If a plurality of LEDs are used as a light, there is also the possibility that these LEDs radiate with different wavelengths and that the duration of radiation and intensity of each individual LED is controlled by the microcontroller.

In the interior of the light source at least one photo sensor can be arranged whose signal is feedable via a signal line associated with the supply line to an evaluation unit arranged in the control unit for switching the light source. The embodiment enables a very advantageous operating mode of the implant system, which is also the subject of the present disclosure. In this way, a theragnostic implant is provided in which it is possible to radiate light of a suitable wavelength by means of the light source by dispensing a substance which accumulates in the tumor and induces fluorescence, and to check the occurrence of fluorescence by means of a filter and photodetector adapted to the wavelength to be detected. If this can be determined by the photodetector, which is formed by the photo sensor and the spatially separately arranged evaluation unit, this is a diagnostic indication of the presence of tumor cells, which indicates the therapeutic use of the implant system by turning on the light source, which activates the phototoxic drug for therapy. When using multiple lights within the light source, it is possible to switch on only the lights facing the tumor cells to optimize energy consumption.

For long-term therapy, a clocked operation is advantageous in which in intervals chosen by the physician and stored in the control unit, which are synchronized with the administration of the drug, the light source is activated to search for fluorescence in order to switch to the therapy mode when fluorescence is detected to generate the phototoxic effect of the intended drug.

Drugs suitable for generating fluorescence are, for example, 5-ALA (am inolaevulinic acid). Porphyrins, cyanins, metatetrahydrophenylchlorines and others are suitable as photosensitive, therapeutically active substances.

The use of a light source made of glass also allows for the diagnostic application of imaging methods for progress monitoring, including MRIs. There is also the possibility of assigning a camera to the light source that is focused on the tumor region, the data of which can be transferred via a camera line, which runs parallel to the supply line, to the control unit 3 and/or can be stored there and/or be wirelessly transferred to an extracorporeal receiver or, with appropriate indication, of again removing the implant system and removing the light source from the resection cavity and carrying out another resection or replacing the light source.

Further scope of applicability of the present invention will become apparent from the detailed description given hereinafter. However, it should be understood that the detailed description and specific examples, while indicating preferred embodiments of the invention, are given by way of illustration only, since various changes, combinations, and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 3 is an isolated view in perspective of a light carrier of a parallelepiped shape comprising a plurality of lights, FIG. 4 is a view corresponding to FIG. 3 with a carrier in the shape of a pyramid, FIG. 5 is a schematic view, open on one side, of the control unit having a plurality of memory cells and a control board having a microcontroller.

DETAILED DESCRIPTION

Figure 1:
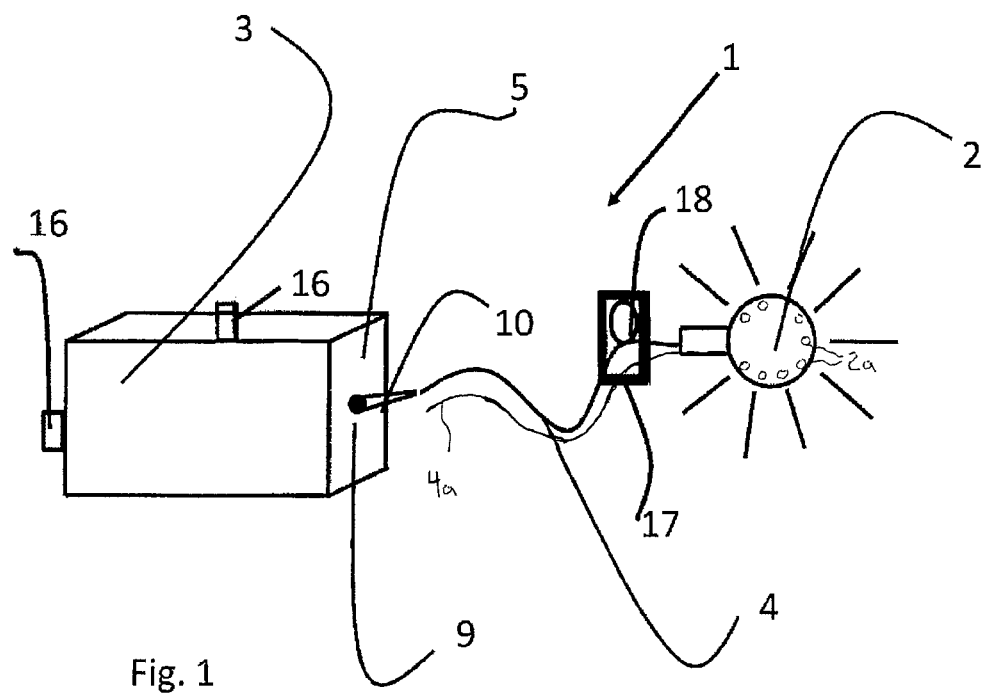
FIG. 1 is a schematic representation of the implant system composed of light source, supply line and control unit.
Figure 2:
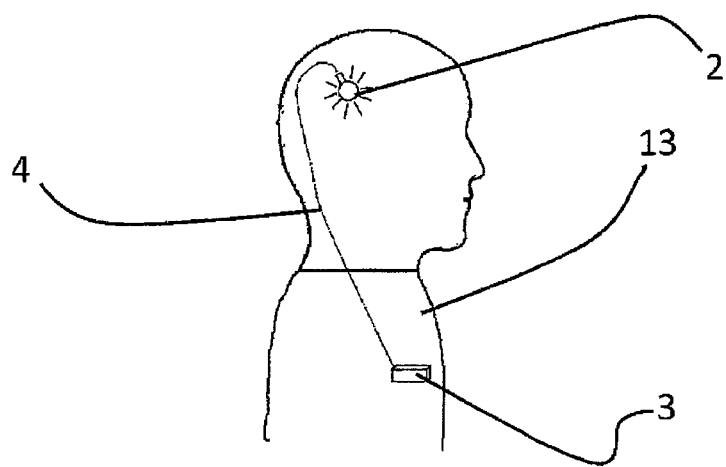
FIG. 2 is a schematic view of the implant system positioned in a human.

FIG. 1 shows an implant system 1 intended for use in photodynamic therapy. This implant system 1 comprises a light source 2 for radiating light which can be implanted in a resection cavity, an autonomous control unit 3 and a supply line 4 for connecting the light source 2 to the autonomous control unit 3.

The autonomous control unit 3 illustrated in FIG. 5 has a housing 5 in which at least one electrical memory cell 6 is arranged, wherein in the illustrated exemplary embodiment a total of 4 electrical memory cells 6 are present embodied as accumulators. Also arranged in the housing 5 is a control board 8 comprising a microcontroller 7. It can also be seen that a coupling link 9 is guided through the wall of the housing 5 to which a coupling link 10 assigned to the supply line 4 can be releasably attached as a counterpart. This supply line 4 is guided to an LED carrier 11, the design of which is chosen in such a way that a uniform spherical illumination is made possible by a plurality of LEDs 12 forming the light source. The use of other lights is also conceivable. FIG. 3 shows the LED carrier 11 in the shape of a cuboid, namely a cube, while FIG. 4 shows the LED carrier 11 in the shape of a pyramid. The LED carrier 11 acts as a connecting link of the LEDs 12 to the supply line 4.

The light source 2 shown symbolized in FIG. 1 consists of two half shells made of glass between which the light source is accommodated, i.e., the LEDs 12 arranged on the LED carrier 11 in the embodiments shown. Other materials for the light source 2 are possible, as long as these are translucent materials. Silicone-based materials and materials of plastic can also be considered, which in particular are biocompatible materials. A masking can be arranged on the light source 2 for the purpose of locally limited shielding for partial illumination.

Figure 6:
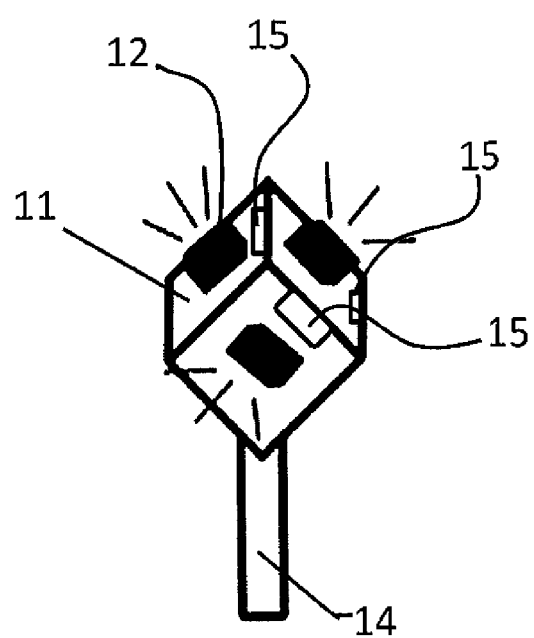
FIG. 6 is a view corresponding to FIG. 3 of an embodiment with a photo sensor.

FIG. 6 shows an embodiment in which the light source 2 on the LED carrier 11 contains at least 1, in the example shown here 4, photo sensors 15, the signal of which can be fed via a signal line assigned to the supply line 4 to an evaluation unit arranged in the control unit 3 for switching the light source 2. This embodiment can be used as a theragnostic implant system in order to initiate the therapeutic use of the implant system after appropriate administration of a fluorescent drug accumulating in the tumor cells and the occurrence of fluorescence as an indication of the presence of tumor cells.

With such an implant system 1, it is possible to insert the light source 2 in the resulting resection cavity after surgical removal of a tumor, in particular a brain tumor or glioblastoma, wherein the supply line 4 is guided from the body, in particular guided out from the skull cap and, for strain relief by means of the line tab 17, is fixed to the skull cap by means of a fastener extending through the opening 18. The supply line is placed subcutaneously in the upper body of the patient 13 using a trocar. There, the supply line 4 is then connected via the coupling links 9, 10 to the housing 5 of the control unit 3, which is connected with the surrounding soft tissues of the body by means of the eyelets 16 in order to prevent it from wandering in the body. This also acts as strain relief for the supply line 4 at the other end facing the control unit 3.

To be able to fill the resection cavity formed during the operation completely up to the resection margin, multiple light sources 2 of different volumes are provided so that a light source 2 of a suitable size can be selected. It is also conceivable to provide light sources 2 with lights of a different radiation frequency in order to optimally enable photoactivation of the drug used.

In addition, there is the possibility that the control unit 3 has a reservoir for drugs, that the reservoir is connected via a drug line with the light source 2 which is set up to dispense the drug to the surrounding tissue and that the drug line 4a runs parallel to the supply line 4 and that the light source 2 has pores and/or channels 2a on its surface for distributing the drug and that the reservoir has a drug absorption path for filling by means of an extracorporeal injection needle. The implant system 1 can also be supplemented such that the light source 2 is assigned a camera focused on the tumor area, the data of which can be transferred via a camera line which runs parallel to the supply line 4, to the control unit 3 and/or be stored there and/or be wirelessly transferred to an extracorporeal receiver.

The correspondingly modularly designed implant system 1 is then put together in a manner customized to the patient by selecting the suitable light source 2 with the assigned supply line and the control unit 3. Since the intention is said system's implantation and for it to permanently remain in the body 13 of the patient, the light source 2 and/or the supply line 4 and/or the control unit 3 are coated with a biocompatible material such as medical grade silicone.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. An implant system for photodynamic therapy, the system comprising:
   a plurality of light sources of different volumes and with lights of different radiation frequency for radiating light that is adapted to be implanted in a resection cavity of a patient; and
   a control unit connectable to the light source via a supply line, the control unit being positioned separate from the plurality of light sources at an exterior of the patient,
   wherein the control unit has a reservoir for a drug,
   wherein the reservoir is connected via a drug line to the plurality of light sources, which is configured to dispense the drug to surrounding tissue,
   wherein the drug line runs substantially parallel to the supply line, and
   wherein each of the plurality of light sources has pores and/or channels on its surface for dispensing the drug.

2. The implant system according to claim 1, wherein the plurality of light sources is made of a translucent material.

3. The implant system according to claim 2, wherein scattering centers for promoting a uniform spherical illumination are formed in the translucent material.

4. The implant system according to claim 1, wherein a masking is provided on the light source for partial illumination.

5. The implant system according to claim 1, wherein each of the plurality of light sources is formed of two half shells, between which at least one light is accommodated, which is connectable by the supply line to the voltage source arranged in the control unit.

6. The implant system according to claim 4, wherein the light is provided in plurality and the plurality of lights are LEDs.

7. The implant system according to claim 6, wherein the arrangement of the LEDs is chosen for a uniform spherical illumination.

8. The implant system according to claim 6, wherein the LEDs are arranged on an LED carrier, which is formed as a connecting link of the LEDs with the supply line.

9. The implant system according to claim 8, wherein the LED carrier has a shape of a sphere or the shape of a cuboid, including the special form of a cube, or the shape of a pyramid, on whose surfaces the LEDs are disposed in a center of gravity.

10. The implant system according to claim 1, wherein the reservoir comprises a drug absorption path for filling via an extracorporeal injection needle.

11. The implant system according to claim 1, wherein two coupling links are provided for the releasable connection of a supply line to the control unit, one of which is arranged at an outer side of a housing of the control unit.

12. The implant system according to claim 11, wherein the plurality of light sources selectively connect one of the light sources via the associated supply line to the coupling link of the control unit.

13. The implant system according to claim 1, wherein the control unit has at least one electrical memory cell for voltage supply to the at least one LED and a control board.

14. The implant system according to claim 1, wherein a housing of the control unit is made from implant steel or titanium or a biocompatible plastic.

15. The implant system according to claim 1, wherein the plurality of light sources and/or the supply line and/or the control unit and/or the drug line are coated with a biocompatible material.

16. The implant system according to claim 15, wherein the biocompatible material is formed from medical silicone.

17. The implant system according to claim 1, wherein, in the interior of the light source, at least one photo sensor is arranged, the signal of which is fed via a signal line assigned to the supply line to an evaluation unit arranged in the control unit for switching the plurality of light sources.

18. The implant system according to claim 1, wherein the plurality of light sources is assigned a camera that is focused on the tumor area, the data of which is transferred via a camera line which runs substantially parallel to the supply line to the control unit and/or is adapted to be stored there and/or is adapted to be wirelessly transferred to an extracorporeal receiver.

19. The implant system according to claim 1, wherein at least one eyelet is formed on the control unit.

20. The implant system according to claim 1, wherein a line tab with an opening is arranged on the supply line in an area facing the plurality of light sources for attachment to the skull cap.

21. The implant system according to claim 1, further comprising:
   an LED carrier, having a plurality of surfaces, the LED carrier having a shape of a sphere, a cube, or a pyramid, disposed within the light source;
   a plurality of LEDs; and
   a plurality of sensors,
   wherein the plurality of LEDs and the plurality of sensors are arranged on each of the plurality of surfaces of the LED carrier.

22. An implant system for photodynamic therapy, the system comprising:
   a plurality of light sources of different volumes and with lights of different radiation frequency, for radiating light, that is adapted to be implanted in a resection cavity of a patient, each of the plurality of light sources comprising pores or channels on a surface of the light source for dispensing a drug to surrounding tissue; and
   a control unit connectable to the plurality of light sources via a supply line, the control unit being positioned separate from the plurality of light sources at an exterior of the patient.

* * * * *